(12) United States Patent
Jamieson et al.

(10) Patent No.: US 6,819,265 B2
(45) Date of Patent: Nov. 16, 2004

(54) ADVANCED WARNING ICE DETECTION SYSTEM FOR AIRCRAFT

(75) Inventors: James R. Jamieson, Savage, MN (US); Mark D. Ray, Burnsville, MN (US)

(73) Assignee: Rosemount Aerospace Inc., Burnsville, MN (US)

( * ) Notice: Subject to any disclaimer, the term of this patent is extended or adjusted under 35 U.S.C. 154(b) by 0 days.

(21) Appl. No.: 10/225,610

(22) Filed: Aug. 22, 2002

(65) Prior Publication Data

US 2004/0036630 A1 Feb. 26, 2004

(51) Int. Cl.[7] .................................................. G08B 21/00
(52) U.S. Cl. ........................................ 340/962; 342/26
(58) Field of Search ............................... 340/962, 580, 340/968; 342/26; 701/14

(56) References Cited

U.S. PATENT DOCUMENTS

| | | | |
|---|---|---|---|
| 3,625,613 A | | 12/1971 | Abell et al. |
| 3,723,007 A | | 3/1973 | Leonard |
| 4,303,862 A | | 12/1981 | Geiger |
| 5,028,929 A | | 7/1991 | Sand et al. |
| 5,546,183 A | * | 8/1996 | Fegley et al. ............... 356/336 |
| 5,557,040 A | | 9/1996 | Inenaga et al. |
| 5,641,972 A | * | 6/1997 | Breda .......................... 250/573 |
| 6,010,095 A | * | 1/2000 | Hackmeister ........... 244/134 F |
| 6,040,899 A | * | 3/2000 | Breda ........................ 356/28.5 |
| 6,052,056 A | * | 4/2000 | Burns et al. ................. 340/583 |
| 6,069,565 A | * | 5/2000 | Stern et al. .................. 340/583 |
| 6,489,915 B1 | * | 12/2002 | Lines et al. .................... 342/26 |
| 6,535,158 B2 | * | 3/2003 | Wilkerson et al. ............ 342/26 |

OTHER PUBLICATIONS

Air/Space–Based Atmospheric Lidars—2002 Optech Incorporated (pp. 1–5), web site publication.
Raman Lidar (RL) Information Updated on Tuesday May 21 17:15:13 2002—RL Instrument (pp. 1–12), website publication.
Goodrich Sensor Systems, Next Generation IceHawk—Wide Area Ice Detection System (pp. 1–4), Brochure.

* cited by examiner

*Primary Examiner*—John Tweel
(74) *Attorney, Agent, or Firm*—Calfee, Halter & Griswold LLP; James M. Rashid, Esq.

(57) ABSTRACT

An ice detection warning system mountable on board an aircraft for inflight monitoring of the airspace ahead of the aircraft comprises: a first plurality of optical elements configured to direct a pulsed laser beam at a first wavelength from a laser source into the airspace ahead of the aircraft; a second plurality of optical elements configured to separate received backscattering of light from the laser beam into a plurality of predetermined wavelengths; a plurality of light detectors for detecting the light of the separated plurality of wavelengths, respectively, and generating respectively corresponding plurality of electrical signals representative of the light detected thereby; and a processor for processing the plurality of electrical signals to determine if airspace conditions ahead of the aircraft are likely to cause ice accretion on the surface of the aircraft, and for generating a warning indicative thereof. In one embodiment, the warning system includes an optical scanner operative to scan the pulsed laser beam into the airspace ahead of the aircraft with a predetermined scan pattern, the scanner also being operative to receive the backscattering of light from the pulsed laser beam and direct it to the second plurality of optical elements which is configured to separate the received backscattering of light into the plurality of predetermined wavelengths.

23 Claims, 9 Drawing Sheets

ADVANCED WARNING ICE DETECTION SYSTEM FOR AIRCRAFT

BACKGROUND OF THE INVENTION

The present invention is directed to ice detection systems, in general, and more particularly, to an advanced warning ice detection system for use on-board an aircraft during flight.

For aircraft application, inflight ice detection is limited to in-situ sensors, like the Ice Detector manufactured and marketed by Rosemount Aerospace, Inc. bearing model no. 871, for example, which is mounted on the aircraft surface to sense a collection of ice on a vibrating element. A ground-based ice detection system known as the IceHawk® system, marketed and manufactured by the Sensor Systems Division of Goodrich Corporation, detects accreated ice on the surface of an aircraft visually by laser polarization scanning techniques. Both of these type systems detect ice after it has accreated on the aircraft surface and thus, requires de-icing to restore the surface to its intended state. Neither system can predict ice accretion prior to the formation on the aircraft surface or before the aircraft enters an icing region of airspace during flight.

A UV Raman LIDAR which is an active, ground-based, laser remote sensing instrument measures vertical profiles of the atmosphere above the site of the instrument for water-vapor mixing ratio and several cloud- and aerosol-related quantities. Such a system, which is known as CART (Cloud and Radiation Testbed), is currently being developed by the Sandia National Laboratories for the atmospheric radiation monitoring (ARM) project and is described at the website <<RL Instrument.htm>>. While operational at a southern great plains site, the ground-based Raman LIDAR instrument remains a test bed for obtaining atmospheric measurements for climate research. It includes a very large sized receiver telescope and laser transmitter to achieve the long range and precision necessary for extensive profiling of the atmosphere.

Accordingly, it is desirable to have a warning system small enough in size to be mountable on-board an aircraft and powered thereby and which has the capability of inflight monitoring the airspace ahead of the aircraft for conditions likely to cause ice accretion on the surface of the aircraft and warn the pilot and crew of such an impending condition in sufficient time to change the heading of the aircraft and avoid the icing region of airspace. It would be also desirable for such a system to be able to share certain elements of one or more existing air data and obstacle awareness measuring systems already on-board an aircraft to reduce the cost, size, weight, and power requirements thereof.

SUMMARY OF THE INVENTION

In accordance with one aspect of the present invention, a warning system mountable on board an aircraft for inflight monitoring of the airspace ahead of the aircraft for conditions likely to cause ice accretion on the surface of the aircraft and provide a warning thereof comprises: a laser source for generating a pulsed laser beam at a first wavelength; a first plurality of optical elements configured to direct the pulsed laser beam into the airspace ahead of the aircraft; a second plurality of optical elements for receiving the backscattering of light from the pulsed laser beam, the second plurality of optical elements configured to separate the received backscattering of light into a plurality of predetermined wavelengths; a plurality of light detectors for detecting the light of the separated plurality of wavelengths, respectively, and generating respectively corresponding plurality of electrical signals representative of the light detected thereby; and a processor for processing the plurality of electrical signals to determine if airspace conditions ahead of the aircraft are likely to cause ice accretion on the surface of the aircraft, and for generating a warning indicative thereof.

In accordance with another aspect of the present invention, the first plurality of optical elements of the warning system is configured to direct the pulsed laser beam along a first optical path; the warning system includes an optical scanner disposed in the first optical path and operative to scan the pulsed laser beam into the airspace ahead of the aircraft with a predetermined scan pattern, the scanner also operative to receive the backscattering of light from the pulsed laser beam and direct said backscattering along a second optical path; and the second plurality of optical elements of the warning system is configured to receive the backscattering of light from the second optical path and to separate the received backscattering of light into the plurality of predetermined wavelengths.

DETAILED DESCRIPTION OF THE INVENTION

Figure 1:
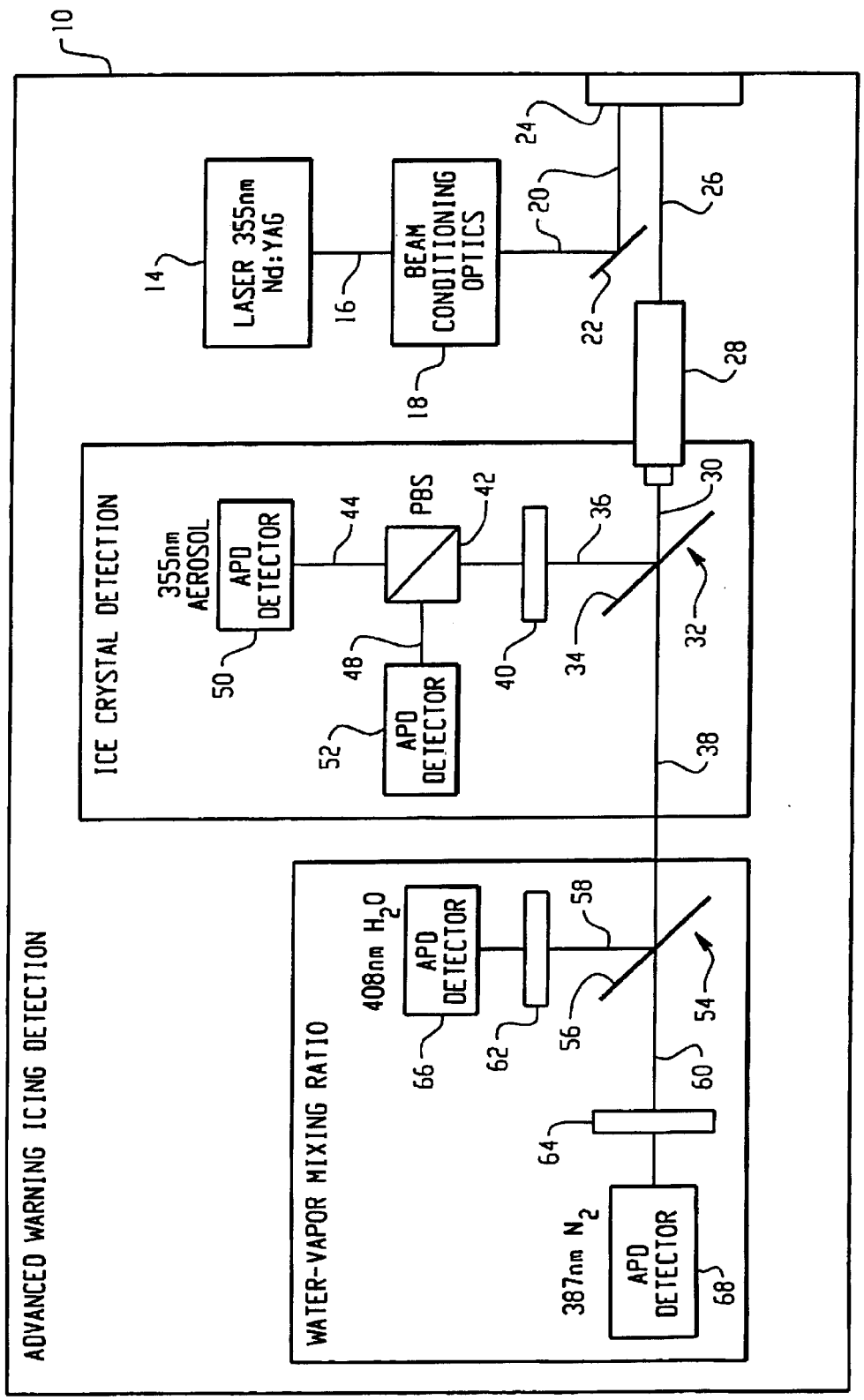
FIGS. 1 and 2 are collectively a block diagram of an advance warning ice detection (AWID) system suitable for embodying the principles of the present invention.
Figure 2:
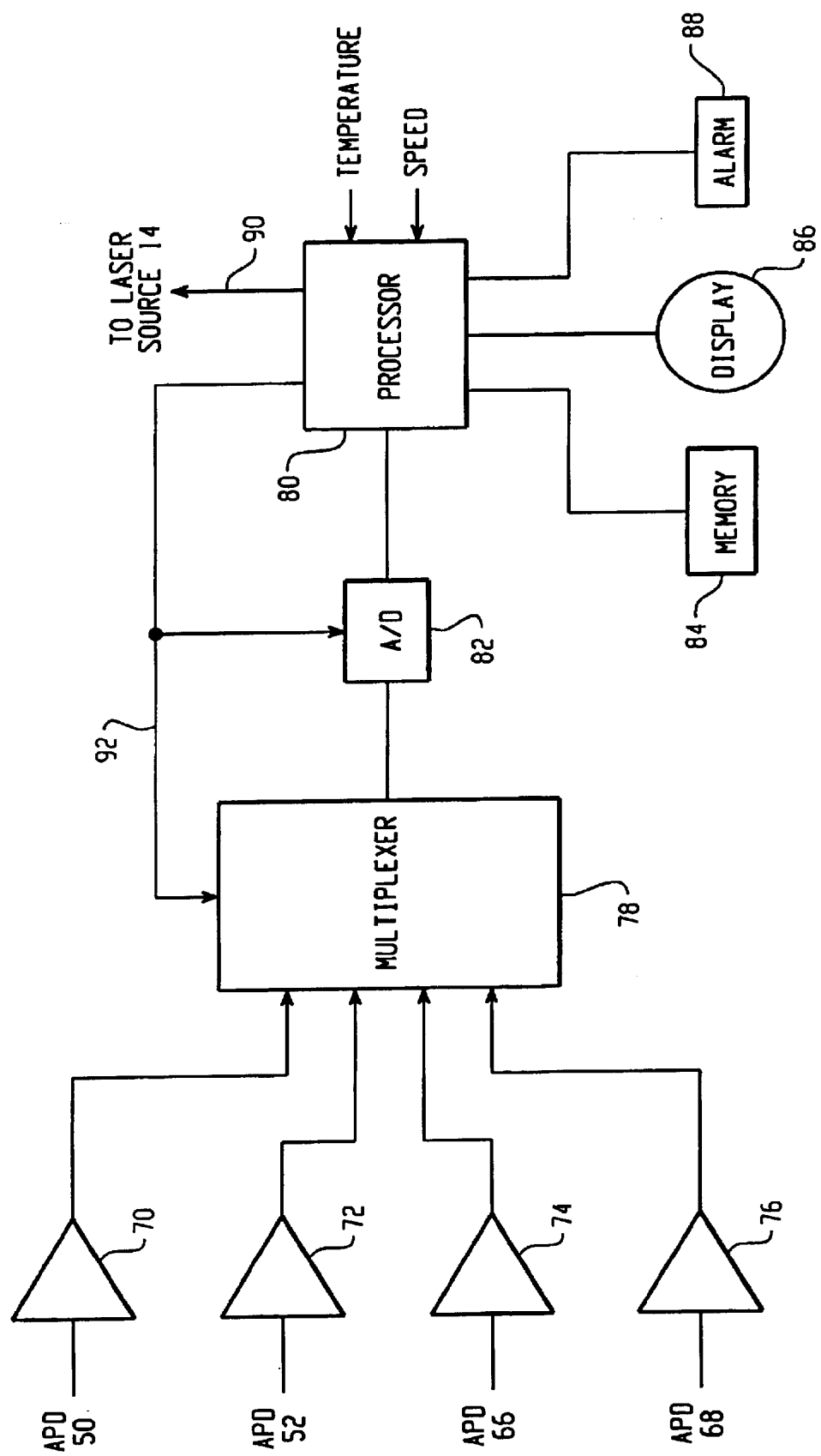
Figure 3:
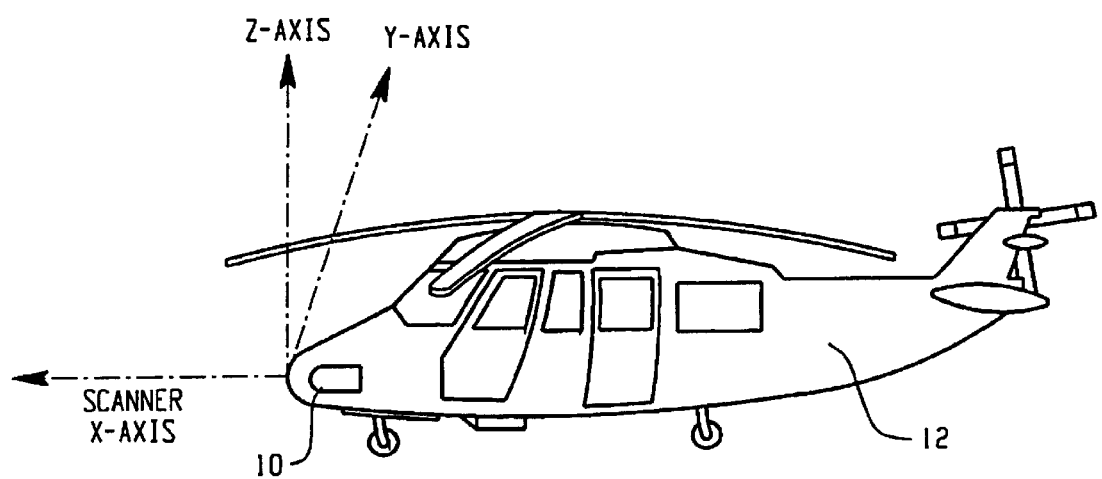
FIG. 3 is an illustration of an exemplary aircraft on-board which the AWID system embodiment may be disposed.

An advanced warning ice detection (AWID) system 10 using Raman LIDAR techniques suitable for embodying the principles of the present invention is shown in the block diagrams of FIGS. 1 and 2. For the present embodiment, the AWID system 10 is disposed on-board an aircraft, like a helicopter 12, for example, as shown in the illustration of FIG. 3. While a helicopter is being used for the present embodiment, this is done merely by way of example, and it is understood that the system 10 may be disposed on any aircraft, rotary or fixed wing, without deviating from the broad principles of the present invention.

Referring to FIGS. 1 and 2, a laser source 14 which may be of a Nd:YAG type is operative to generate along an optical path 16 laser pulses preferably at a wavelength of substantially 355 nanometers (nm), 3rd harmonic, and at a pulse repetition rate of 20–30 pulses per second. The laser source 14 for the present embodiment is of the type manufactured by Big Sky under the model no. CFR400, for example, which generates pulses of 150 millijoules. Beam conditioning optics 18 may be disposed in the optical path 16 for reducing the laser beam divergence and directing the laser pulses along an optical path 20. An optical element 22, like a folding mirror, for example, may be disposed in the path 20 to direct the laser pulses through a window 24 of the system 10 and into the airspace ahead of the aircraft, preferably substantially along the heading of the aircraft or X-axis as shown in FIG. 3. The material of the window for the present embodiment may be fused silica to pass the laser wavelengths in the ultraviolet (UV) range. The beam width of the laser pulses at the system exit point is approximately 25 millimeters (mm), for example, and diverges conically at a maximum angle α to the projection axis, which may be on the order of 0.5 millirads, for example, to a diameter of approximately 0.5 meter at a distance of one kilometer (km) from the system.

There are two types of back scatterings that result from the laser pulses. The first type is known as elastic and is caused by reflections of the pulses from aerosol, water or ice particles in the airspace covered by the cone of the diverging laser pulses. In this first type of back scatterings, light is unshifted from the original wavelength. The second type is know as inelastic and is caused by molecular interaction with the laser pulses. In this second type, when the laser pulses strike a molecule of air or water vapor, the wavelength of the pulse is shifted. For example, for molecules of water ($H_2O$) in vapor or ice stages, the wavelength of the back scatterings change to 408 nm, and for nitrogen ($N_2$), the wavelength of the back scatterings change to 387 nm. Also, the reflections from water and ice particles differ in light polarization. Accordingly, if the reflections at 355 nm are separated by polarization and a photon quantity of each polarization is measured, a ratio of the polarization quantities may be used to determine if water or ice crystals are present in the conical region of the laser pulses ahead of the aircraft.

Referring to FIG. 1, back scatterings from the laser pulses enter the system 10 through window 24 and are guided along optical path 26. A telescope 28 may be disposed in the optical path 26 to collect the back scatterings of light and converge and focus the light to a substantially narrow beam which is guided along an optical path 30. A first dichroic optical filter element 32 is disposed in the path 30 and has a surface 34 coated with a special dielectric coating which may be magnesium fluoride, for example. Back scattered light impinging on the surface 34 which has wavelengths in a narrow band around 355 nm is reflected from the surface 34 along an optical path 36 and the remaining back scattered light is passed through the dichroic filter element 32 along an optical path 38.

Disposed in the optical path 36 is an optical filter element 40 which may be a multilayer dielectric bandpass filter, for example, which acts to narrow the bandwidth of wavelengths of the light passed thereby. Downstream of the filter element 40 is a polarization beam splitter 42 which splits the light along path 36 into two optical paths 44 and 48 based on the polarization states thereof. Light along paths 44 and 48 are guided to and measured by light detectors 50 and 52, respectively. Light detectors 50 and 52 may be avalanche photodiodes (APDs), for example, which output an electrical signal representative of the light measured thereby. Alternatively, light detectors 50 and 52 may be photon multiplier detectors of the type manufactured by Hamamatsu under the model no. R3809U, for example, which have the ability to count the photons of light measured thereby over a predetermined time interval and generate an electrical signal representative thereof.

A second dichroic optical filter element 54 is disposed in the path 38 and has a surface 56 coated with a special dielectric coating which may be magnesium fluoride, for example. The thickness and/or number of layers of the coating may be different from that of the dichroic element 32. Back scattered light impinging on the surface 56 which has wavelengths in a narrow band around 408 nm is reflected from the surface 56 along an optical path 58 and the remaining back scattered light which has wavelengths in a narrow band around 387 nm is passed through the dichroic filter element 54 along an optical path 60. Disposed in the optical paths 58 and 60 are optical filter elements 62 and 64, respectively, which may be a multi-layer dielectric bandpass filter, for example, and act to narrow the bandwidth of wavelengths of the light respectively passed thereby.

Light beams along paths 58 and 60 downstream of the filter elements 62 and 64 are guided to and measured by light detectors 66 and 68, respectively. Light detectors 66 and 68 also may be avalanche photodiodes (APDs), for example, which output an electrical signal representative of the light measured thereby. Alternatively, light detectors 66 and 68 also may be photon multiplier detectors of the type manufactured by Hamamatsu under the model no. R3809U, for example, which have the ability to count the photons of light measured thereby over a predetermined time interval and generate an electrical signal representative thereof. The optical paths described herein above may be in air or guided within fiber optic cables, or a combination of the two.

Electrical signals from the light detectors 50, 52, 66 and 68 are coupled to signal conditioning circuits 70, 72, 74 and 76, respectively, as shown by the exemplary schematic block diagram of FIG. 2. The signal conditioning circuits may include amplification circuitry, circuitry to further filter out electrical noise and/or to integrate the signals from the light detectors over a predetermined interval of time which are well-known to all of those skilled in the pertinent art. In the present embodiment, the outputs of the signal conditioning circuits 70, 72, 74 and 76 are coupled to respective inputs of a multiplexer circuit 78. The output of circuit 78 is coupled to a processor 80 through an analog-to-digital (A/D) converter 82, if needed. The processor 80 includes a memory unit 84 to store information taken in thereby which may thereafter be accessed and processed in accordance with certain processing algorithms, the digital code of which also may be stored in the memory unit 84. In some applications, the processor 80 may provide the results of its processing to a display unit 86 and/or to alarm indicators 88 located in the cockpit of the aircraft. Moreover, the processor 80 may be coupled to address inputs of the multiplexer 78 and control inputs of the A/D converter 82 over signal lines 92 and also may be coupled to the laser source 14 over a signal line 90. It is understood by all those skilled in the pertinent art that other circuit arrangements are possible without deviating from the broad principles of the present invention.

Depending on the programmed algorithms, the processor 80 may drive the laser source 14 over signal line 90 to generate laser pulses periodically at say 20 pulses per second, for example. Thus, the processor 80 inherently knows the time that each laser pulse is generated and can keep track of the interpulse period of each pulse during which it can measure any back scatterings from the respective laser pulse. After a predetermined time interval from each pulse, the processor 80 may read in each of the signals from the light detectors 50, 52, 66, and 68 by addressing the multiplexer 78 and controlling the digitization of the selected signal via the A/D converter 82. The digital signals read in by the processor 80 which are representative of the quantity of back scattered light measured by the detectors may be processed "on the fly" or stored in the memory unit 84 for later processing. The light quantity signals from the light detectors may be denoted by certain symbols. For example, the light quantity signal from detector 50 may be denoted as $S_{O1}$, from detector 52 denoted as $S_{O2}$, from detector 66 denoted as $S_{H2O}$, and from detector 68 denoted as $S_{N2}$.

The processor 80 may process the light quantity signals read in to generate the following ratios: $S_{O1}/S_{O2}$, $S_{H2O}/S_{N2}$, and $S_O/S_{N2}$, where $S_O$ may be the sum of $S_{O1}$ and $S_{O2}$. The ratio of $S_{O1}$ to $S_{O2}$ compares the light quantities of the polarization states of the elastic or reflective back scatterings to determine if ice crystals or water vapor is present in the region of airspace ahead of the aircraft being monitored by the laser pulses. If this ratio is at or near unity, then ice crystals are considered present in the monitored region. Otherwise, water vapor or some other aerosol particles are present. The ratio of $S_O$ to $S_{N2}$ is a normalizing measurement of how much aerosol is detected in the monitored region. For example, if ice crystals are determined to be present from the ratio of $S_{O1}$ to $S_{O2}$, then the ration of $S_O$ to $S_{N2}$ is a measure of the ice crystal content. Finally, the ratio of $S_{H2O}$ to $S_{N2}$ is a measure of water vapor to dry air in the monitored region which can be used to determine the likelihood that icing will occur while flying in the region, i.e. an icing region. For example, in helicopter applications, it is known that icing may occur for liquid water content ranging from 0.02 to 2 grams $H_2O$ per cubic meter of air or 0.015 to 1.5 grams $H_2O$ per kilogram of air (at normal temperature and pressure). Accordingly, from the light quantity readings coupled with speed and temperature measurements which are customarily measured or computed on-board an aircraft, the processor 80 may determine not only the likelihood of icing, but also the rate of icing accretion, prior to entering an icing region. As these determinations are made by the processor 80, it may provide warning or alarm indications via indicators 88 or display visual or text messages to the pilot and crew via the display 86.

More specifically, the processor 80 determines a measure of the liquid water content (LWC) in the monitored region of space ahead of the aircraft by measuring the fraction of droplets which have frozen into ice crystals. The fraction of ice crystals present in this region also provides a rough estimate of the temperature thereof. In addition, it yields qualitative information about the potential severity of icing since ice crystals do not adhere to the surfaces of aircraft as readily as droplets of freezing water. Hence, a region containing mostly ice crystals may be safe to traverse with an aircraft.

Given the LWC measurement as described above, the processor 80 receives and captures the air temperature and the speed of the aircraft measurements from a flight computer or other sources to calculate the probability or likelihood of icing. For an airfoil moving through moisture-laden air, the airfoil's water catch or icing accretion rate $M_T$ is determined by the following formula:

$$M_T = 0.3296 \cdot E_M \cdot V \cdot LWC \cdot t \cdot C,$$

where:

$M_T$ is the mass of water intercepted (in lb/hr/ft of airfoil span), $E_M$ is the collection efficiency of the airfoil (measured in percent)

LWC is the measurement of liquid water content (g/m$^3$),

V is the measurement of velocity of the aircraft (miles/hr), t is the airfoil thickness (percent of the chord length, and C is the chord length of the airfoil (feet).

The constant 0.3296 is a conversion factor appropriate for the particular choice of units and may be pre-stored in memory 84 along with the constants t and C and accessed for use in the above calculation. The collection efficiency $E_M$ is the ratio of the mass of liquid water collected by the airfoil surface to the mass of liquid water contained in a volume swept by the airfoil. It is a function of the angle of attack, flight speed, droplet size (mean droplet diameter), airfoil shape, ambient temperature, and air pressure. The collection efficiency of an airfoil is determined by analysis or test. After this has been determined for a particular aircraft, it may be pre-stored in the memory 84 and accessed for use into the equation above to estimate the icing accretion rate $M_T$.

Droplet diameters of 20 microns are typically used to determine water catch rates. However, for the calculation of impingement limits, the assumed drop diameter may be 50 microns, for example. These large drops represent a "worst case", since their large mass prevents them from easily slipping past the leading edge of the airfoil. Since the processor 80 does not explicitly measure the mean droplet diameter for the calculation of EM, assuming values of 20 and 50 microns provides typical and worst case ice accretion rates.

Figure 4:
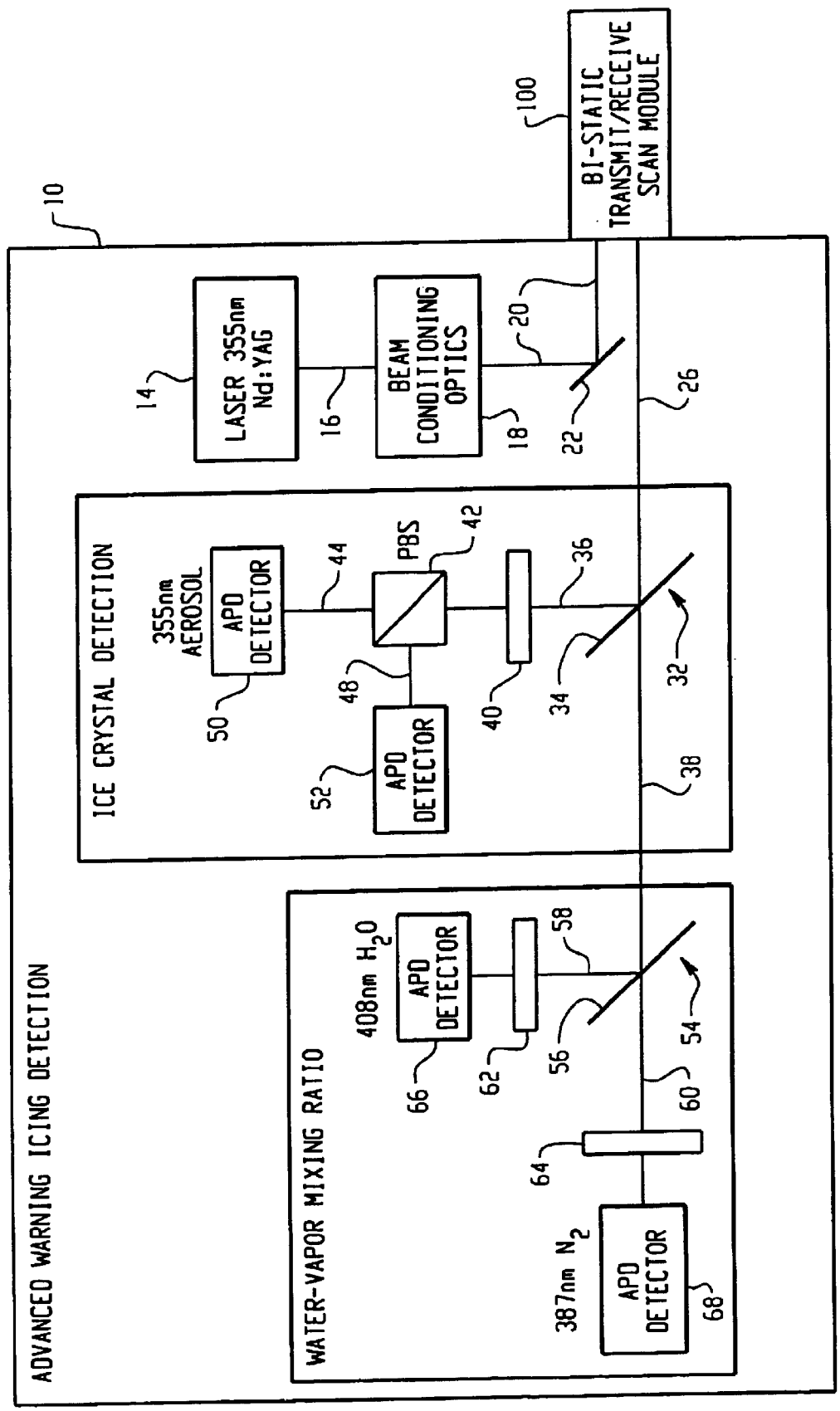
FIG. 4 is a block diagram of an alternate embodiment of the AWID system.

The foregoing described embodiment projects a beam substantially along the heading of the aircraft which diverges conically to a diameter of approximately 0.5 meters at a distance of a kilometer from the aircraft. While this embodiment is appropriate for the detection of an icing region ahead of the aircraft, the pilot may want to know a suitable flight egress route to change the aircraft heading to avoid icing regions ahead of the aircraft. Accordingly, an alternate embodiment of the present invention may include a scan module 100 at the transmit/receive point of the AWID system 10 as shown in the block diagram schematic of FIG. 4, for example. The scan module 100 may be of the bistatic type in which the transmitted beam may be guided over a separate optical path 20 from the path 26 of the received back scatterings. Like reference numerals will be maintained for those elements in the embodiment of FIG. 4 already described for the embodiment depicted in FIG. 1.

Figure 5:
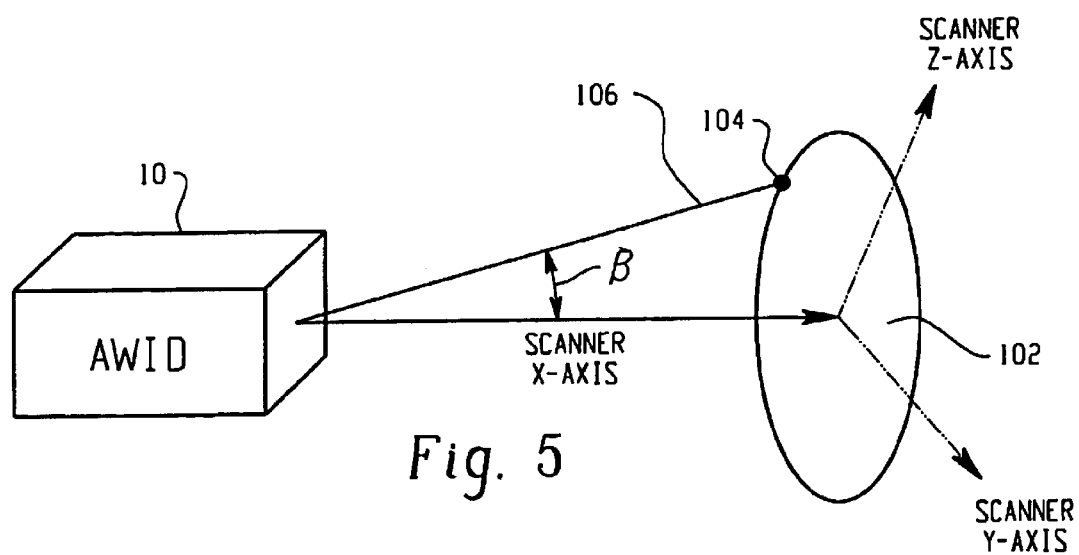
FIG. 5 is a sketch illustrating an exemplary laser beam scan of an AWID system embodiment.

As shown by the exemplary illustration of FIG. 5, the scan module 100 of the AWID system 10 may project a beam 106 in a predetermined pattern to cover an area 102 of airspace ahead of the aircraft beyond that which is covered by the diameter 104 of the beam itself. In the illustration of FIG. 5, the predetermined pattern is substantially circular about an angle β, which may be on the order of five degrees (5°) from the scanner X-axis, for example. Thus, at a kilometer from the aircraft, the beam scan may cover an area of approximately 350 meters in the Y-Z axis plane ahead of the aircraft. It is understood that the scan module 100 may be configured to scan the beam with any number of different scan patterns. Thus, this aspect of the present invention should not be limited to any specific scan pattern. Scanning the beam pattern in azimuth about the heading or X-axis of the aircraft, like on the order of ±90°, for example, will cover for sensing purposes additional airspace ahead of the aircraft. The scan module 100 may additionally scan the beam pattern in elevation to the aircraft heading.

Figure 6:
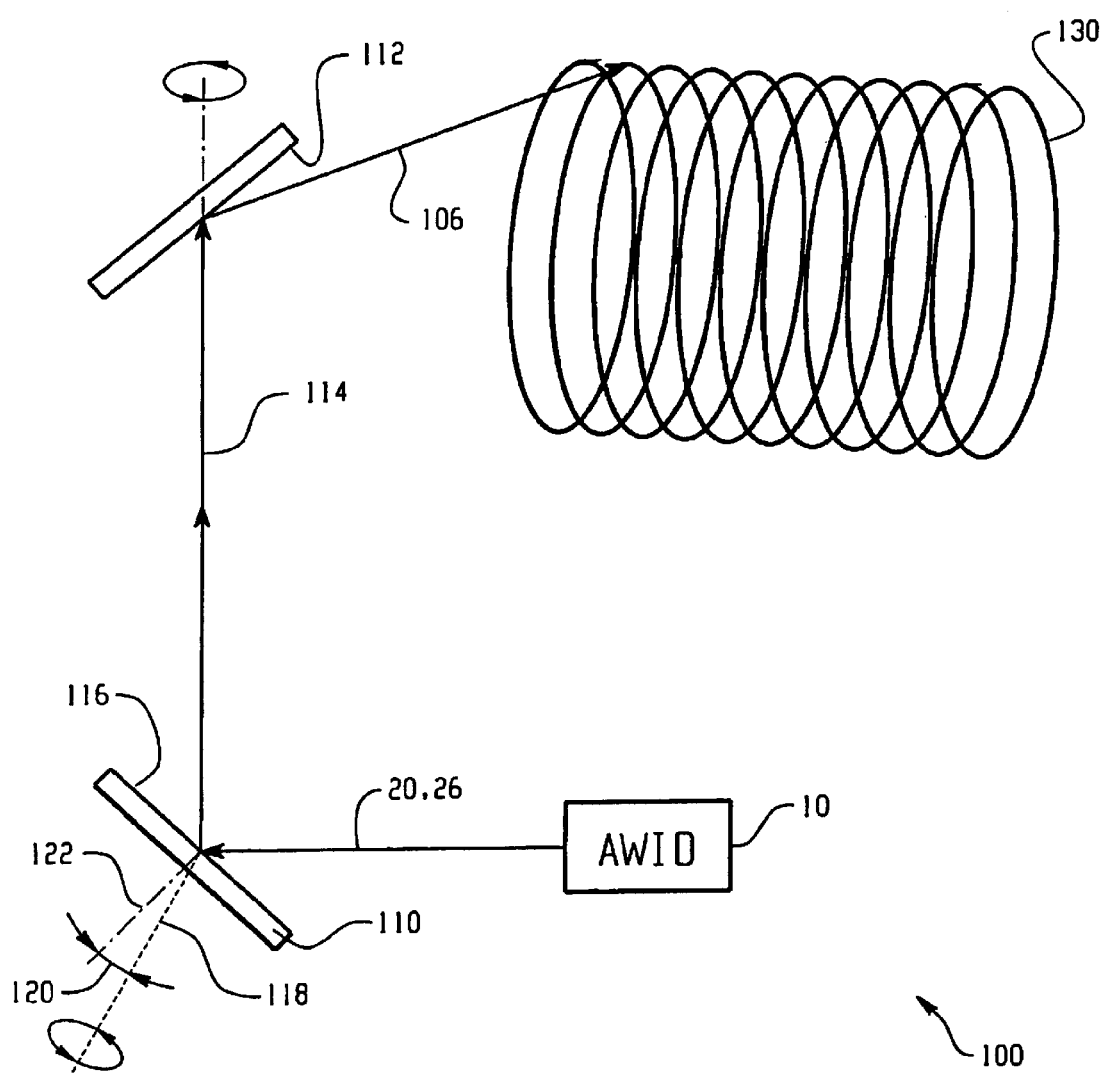
FIG. 6 is a diagram of an exemplary scan module of an AWID system.

An exemplary embodiment of a scan module 100 suitable for use by the AWID system 10 is shown in the illustration of FIG. 6. Referring to FIG. 6, in the present embodiment, the scan module 100 comprises a first rotationally operated optical element 110 for receiving the pulsed laser beam from the optical path 20 and directing it to a second rotationally operated optical element 112 along optical path 114 with the predetermined pattern as will become more evident from the following description. The second element 112 receives the pulsed light beam from the first element 110 and directs the received beam with the predetermined pattern azimuthally over a wide field which may be on the order of plus and minus ninety degrees or so with respect to the X-axis or heading of the aircraft. Back scatterings from aerosols along the predetermined pattern are directed from the second element 112 to the first element 110 over the optical path 114. One or both of the elements 110 and 112 may be configured as fold mirrors.

The optical element 110 may be a wobble mirror rotated about an axis 118 at a predetermined nutation angle 120 from its normal axis 122 (e.g. a Palmer scan mirror), for example, wherein the pulsed laser beam may be reflected from the mirrored surface 116 of the optical element 110 with the predetermined pattern. In an alternate embodiment, a rotating optical wedge which has one surface inclined at a predetermined angle relative to an opposite surface and is rotated about an axis normal to the opposite surface may be substituted for the wobble mirror 110.

In either case, the rotating optical mirror 110 may be coupled to and driven by a conventional circular scan module 124 (see FIG. 7) which may include a drive system, like an electric motor, for example (not shown). In the present embodiment, the element 110 with its drive module 124 may be a Palmer mirror assembly, for example, wherein the drive module rotates the element 110 about its intended axis 118 at an angular speed of approximately one cycle per second, for example, which creates a cyclical conical pattern of pulsed laser beam projected from the AVID system 10 via element 112. Element 112 may also be a mirrored optical element which is driven by an azimuth scan motor 126 (see FIG. 7), which may be a stepper motor, for example, to rotate and scan the conical pattern of the element 110 azimuthally through an arc of approximately 180°, i.e. ±90° or so with respect to the reference or X-axis of the aircraft, over a time period of ten seconds, for example. Thus, the predetermined pattern will include an elevation variation in relation to a X-axis of the scanner. An exemplary scan pattern at two hundred meters (200 m) from the system is illustrated at 130. The helical-like line 130 represents the scan pattern as it is being rotated by the first element 110 and scanned azimuthally by the second element 112. Note that with each scan pattern cycle of the illustration of FIG. 6, the light beam pattern 130 moves in elevation in relation to the Y-axis and in azimuth in relation to the Z-axis. Also, since the pattern 130 takes approximately ten seconds to complete a cycle and since the AWID system 10 generates a light beam pulse every fifty milliseconds (50 ms), then there would be approximately two hundred (200) light beam pulses uniformly generated per scan pattern cycle. As will become more evident from the following description, the AWID system 10 of the present embodiment may determine a location of the back scatterings along the path of the predetermined scan pattern 130 in range, azimuth, and elevation.

As indicated above, back scatterings are directed from the second element 112 to the first element 110 over the optical path 114, and then from element 110 over a bistatic optical path which includes the transmission path 20 and the reception path 26. In the present embodiment, the bistatic path may include a bundle of fiber optic cables, some of which being used for the transmission path 20 and at least one being used for the reception path 26. Thus, upon entering the AWID system 10, the at least one fiber optic cable embodying the path 26 is(are) split from the fiber optic cables embodying the path 20 and the backscatterings along path 26 are directed to the telescope 28, if used in the present embodiment, or directly to the dichroic filter 32.

Figure 7:
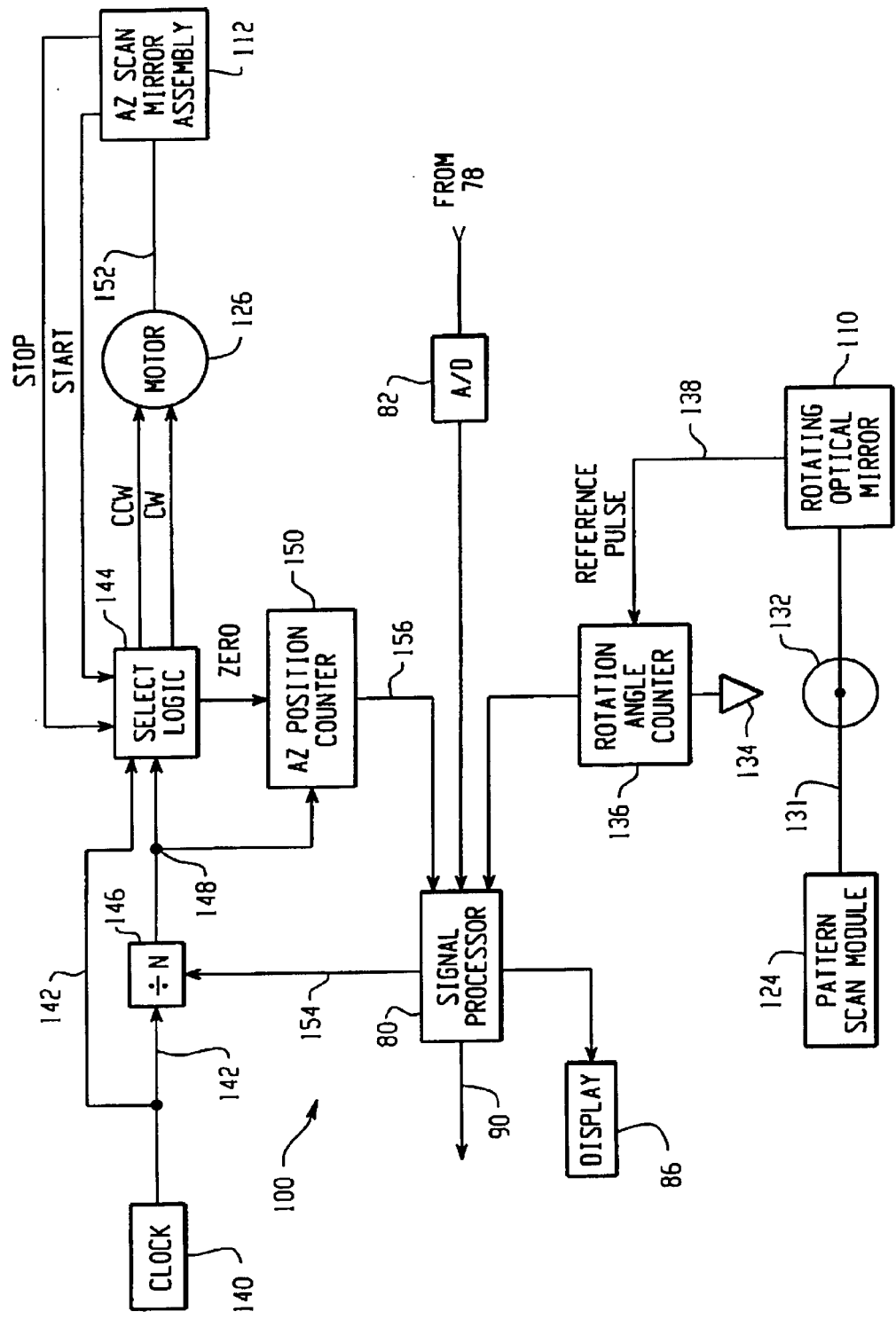
FIG. 7 is a block diagram schematic of an exemplary laser beam scan pattern generator/receiver suitable for use in an embodiment of an AWID system.

A block diagram schematic of a light beam scan pattern generator/receiver suitable for use in the scan module embodiment of FIG. 6 is shown in FIG. 7. Referring to FIG. 7, the scan pattern module 124 may be coupled to and drive the rotationally operated optical element 110 through a shaft 131 which may include an indication of its angle position with respect to a reference angle. In one embodiment for sensing the angular position of the optical element 110, the shaft 131 may be marked with indicia representative of its relative angle or include a wheel 132 thereon or attached thereto with such angle markings. In either case, the indicia may be read by a conventional reader and digitally provided to the processor 80 as a measure of the angle of rotation of the scan pattern optical element. Thus, the processor 80 will have stored at any time the measured angle of the scan pattern which it may use to calculate azimuth and elevation of a detected obstacle.

In another embodiment, the shaft 131 may include markings like grooved teeth, for example, or have affixed thereto the wheel 132 with teeth grooved therein. A conventional proximity device 134 may detect each grooved tooth and generate an electrical pulse in response. These electrical pulses may be counted in a counter 136 which count may be a measure of the current scan pattern angle of optical element 110. The element 110 may include a mechanical, proximity or optical switch positioned to generate a reference pulse 138 each time the element 110 is rotated past the reference angle. The reference pulse 138 may be coupled to the counter 136 to reset it to zero so that it may start counting with respect to the reference angle with each rotation cycle. Accordingly, at predetermined times, like when a laser pulse is generated via control signal 90, for example, the processor 80 may read the contents of the counter 136 which is a measure of the angular position of the optical element and from which the processor 80 may determine elevation at the time the laser pulse is transmitted.

The embodiment of FIG. 7 also exemplifies a way for determining substantially the azimuth position of the directed pulsed laser beam at the time it is transmitted, for example. Referring to FIG. 7, a conventional digital clock circuit 140 generates a clock signal 142 at a predetermined rate. Signal 142 is coupled to select logic circuitry 144 and to a rate divider circuit 146 which divides the rate of clock signal 142 by a factor N. The divided rate signal 148 from the circuit 146 is coupled to the select logic circuitry 144 and to an azimuth position counter 150 which increases its count with each received pulse. The select logic circuitry 144 generates a clockwise signal (CW) and a counter-clockwise signal (CCW) for use in controlling the electric motor 126, which may be a stepper motor, for example. The motor 126 is coupled to the azimuth scan mirror assembly 112 by a shaft 152 for rotating the mirrored element 112 through its 180° rotation. The azimuth mirror assembly 112 may include a first switch positioned to activate and generate a START signal at substantially the 0° azimuth position, and a second switch positioned to activate and generate a STOP signal at substantially the 180° azimuth position, for example. The START and STOP signals are provided to the select logic circuitry 144. In some applications, the signal processor 80 may be coupled to the divider circuit 146 over signal line 154 for setting the number N by which the rate of signal 142 will be divided. The signal processor 80 is also coupled to the counter 150 over signal line 156 for reading the azimuth position count thereof.

In operation, the signal processor 80 may set the number N of the divider 146 which ultimately sets the rate at which the laser beam scan pattern is rotated azimuthally. It is understood that this number N may be preprogrammed into the rate divider circuit 146 as well. So, the select logic 144 receives both a fast rate signal 142 and a slower rate signal 148 and selects one of the rate signals to control or step the motor 126 through its rotation. For example, when the select logic 144 receives the START signal from the scan mirror assembly 112, it selects the slow rate signal 148 to control the motor 126 via the CW control line to rotate clockwise through its 180° rotation in a predetermined time, like ten seconds, for example. When the STOP signal is generated, the select logic 146 responds by selecting the fast rate signal 142 to control the motor 126 via the CCW signal to rotate counterclockwise back to its starting position whereupon the process is repeated. It is understood that the azimuth scan may be controlled to rotate at the slower rate in a counter-clockwise rotation and returned to its starting angular position at a much faster rate as well without deviating from the broad principles of the present invention.

Each time the select logic receives the START signal, it generates a ZERO signal to the counter 150 for resetting the count thereof to zero. The STOP signal may be also coupled to the signal processor 80 which responds to the signal by reading and storing the total count in the counter 150 which is representative of an azimuth angular position of 180°, for example. So, each time a laser pulse is generated, the signal processor 80 may read the concurrent count in the azimuth position counter 150 and use the read count together with the total count to determine the azimuth position of the generated pulse. In the present embodiment, the circuits 140, 144, 146 and 150 may be part of the signal processing circuitry of the scan module 100. It is understood that the functions of these circuits may also be programmed into the signal processor 80.

In some applications, the azimuth scan may be controlled to rotate at the programmed rate for both of the clockwise and counterclockwise directions in which case, the counter 150 will count up from the starting position in one direction and count down from the stop position in the opposite direction. In these applications, the counter may still be reset to zero by the select logic 144 in response to the START signal and the processor 80 may read the total count of the counter 150 in response to the STOP signal. And, similarly, each time a pulse is generated, the signal processor 80 may read the concurrent count in the azimuth position counter 150 and use the read count together with the total count to determine the azimuth position of the generated pulse. A more detailed description of a scanning module and its operation is found in the copending patent application Ser. No. 09/946,057, filed Sep. 4, 2001 and entitled "Combined LOAS and LIDAR System", which is assigned to the same assignee as the instant application and which is incorporated by reference herein in its entirety to provide such details.

Figure 8:
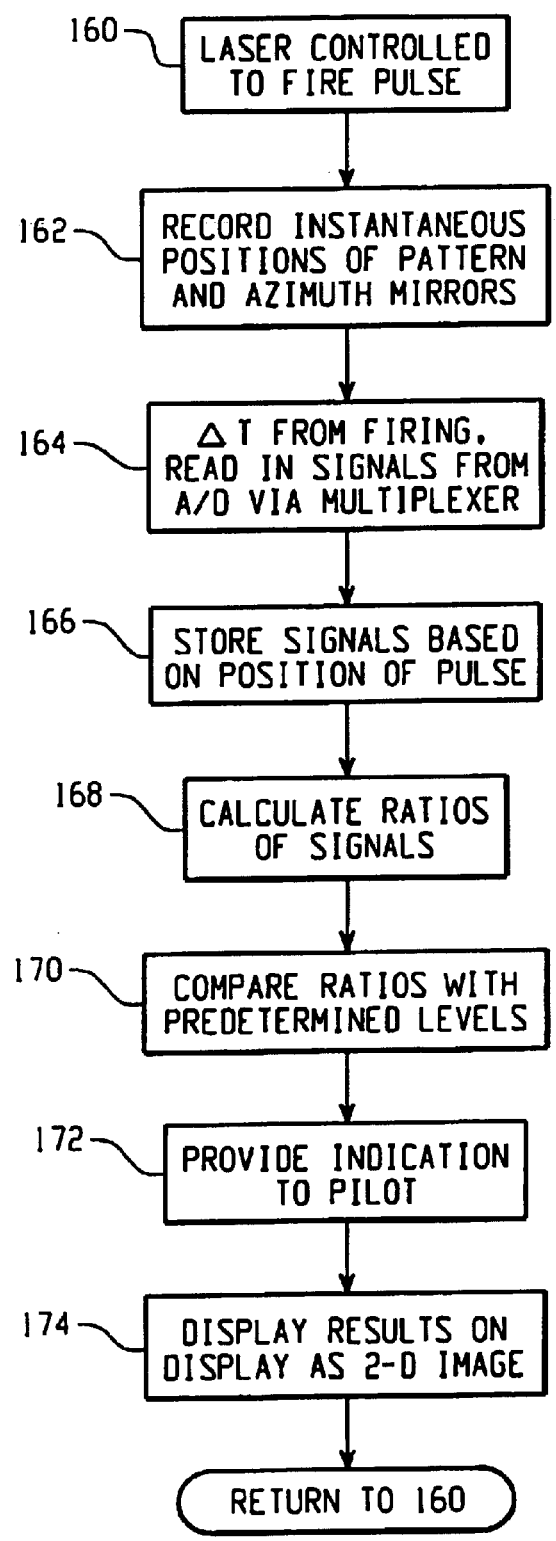
FIG. 8 is a flowchart illustrating a programmed operation of a signal processor suitable for use in an embodiment of an AWID system.

The flowchart of FIG. 8 illustrates a programmed operation of the signal processor 80 by way of example. Referring to FIG. 8, the laser source 14 may be controlled to fire periodically at a rate of 20 pulses per second, for example, with an interpulse period of 50 milliseconds by the programmed processor 80 as shown by the block 160. Then, the processor 80 starts an internal timer. Thereafter, in block 162, the instantaneous positions of the scan pattern and azimuth mirrors are recorded as described supra, preferable in designated locations of memory 84 indexed to the respective generated pulse. After a predetermined time ΔT from the generated pulse, the processor 80 reads in the signals from the light detectors via A/D converter 82 and multiplexer 78 (see FIG. 2) in block 164 and stores the signals in locations of memory 84 indexed to the respective pulse in block 166.

During the interpulse period between generated pulses, the processor 80 may calculate in block 168 the ratios $S_{O1}/S_{O2}$, $S_{H2O}/S_{N2}$, and $S_O/S_{N2}$ as described herein above. The computed ratios may also be stored in locations of memory 84 indexed to the respective generated pulse and its location in azimuth and/or elevation. Then, in block 170, the ratios are compared with respectively corresponding predetermined levels and used along with the relevant stored constants and captured measurements in the computation as described herein above to establish the likelihood of icing and/or the rate of icing accretion in the monitored region of airspace ahead of the aircraft at the recorded location in azimuth and/or elevation. This likelihood and/or rate value may also be stored in a location of memory 84 indexed to the respective generated pulse. As determined from the comparisons, the processor 80 may provide indications to the pilot in block 172 as to the likelihood and/or rate of icing conditions in the region in which the pulse is directed. After block 174, the processor 80 may return processing to block 160 for the generation of the next pulse at a new scan position. Once the processor has completed a look ahead scan in azimuth, likelihoods from the entire scanned airspace of the laser beam may be plotted as a 2-D image in the Y-Z plane, for example, on a screen of the display 86 with the different levels of likelihood of icing conditions color coded in block 174. Accordingly, the pilot can determine from the alarm indications and display an alternate heading for the aircraft to avoid an icing region or at least minimize the likelihood of icing conditions.

Figure 9:
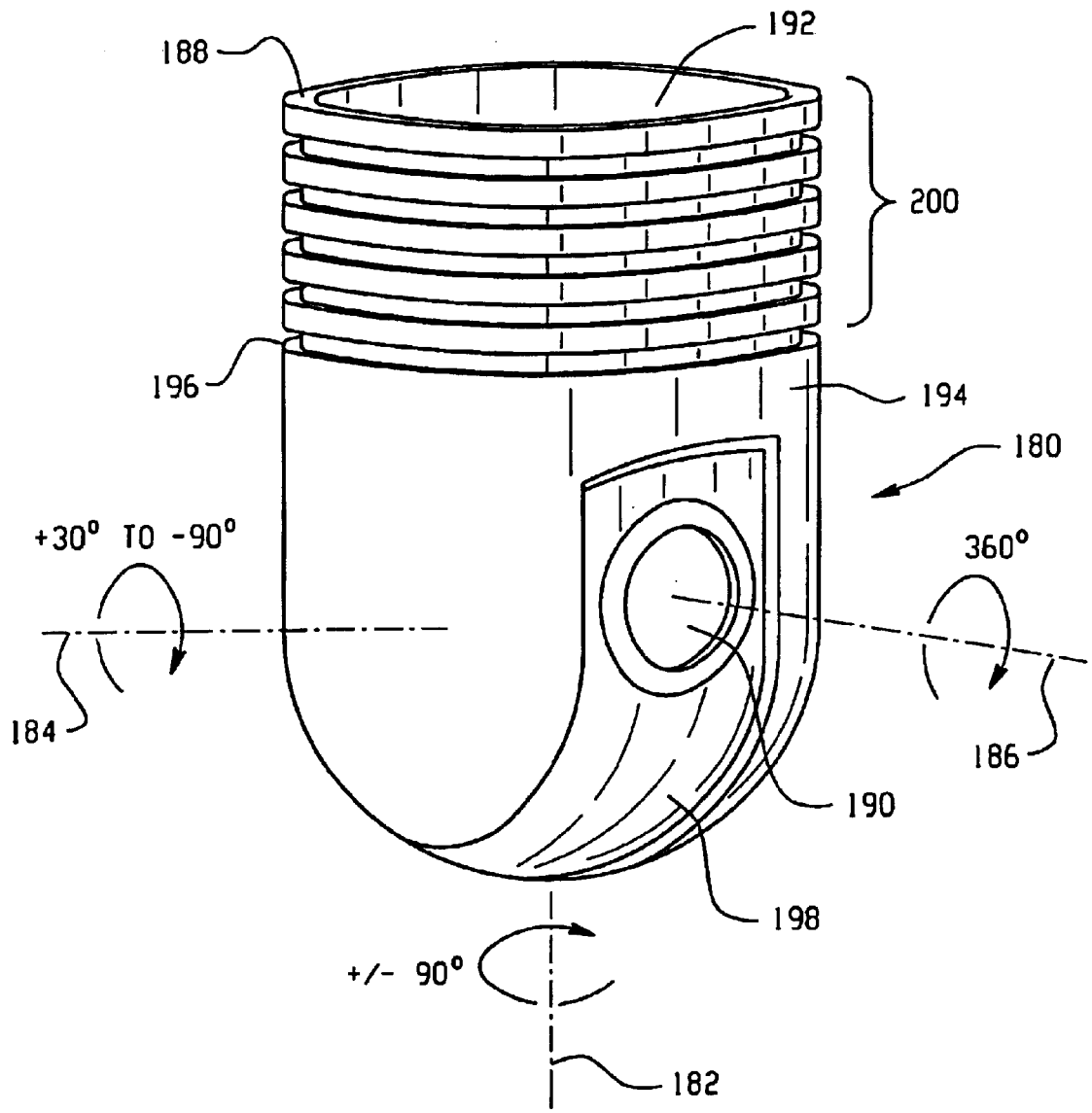
FIG. 9 is an illustration of a scan head suitable for use as a scan module for an embodiment of an AWID system.

Alternatively, the scan module 100 may be embodied in a scan head 180 remotely located from the optical elements of the AWID system 10. An exemplary illustration of a suitable scan head 180 is shown in FIG. 9. In this embodiment, the optical elements of the AWID system 10 may be disposed within the aircraft and well supported and protected from the outside environment. A fiber optic cable bundle may be used for the optical paths 20 and 26 coupling the scan head 180 to the AWID system 10 as was previously described for the embodiments of FIGS. 1 and 4. The fiber optic cabling for the optical paths 20 and 26 may take a circuitous route within the vehicle to reach the scan head 180 which may be mounted to an external surface of the aircraft to permit the beam scan patterns to be projected out from the aircraft as described herein above. More than one scan head may be used in the present embodiment without deviating from the principles of the present invention.

A suitable embodiment of the scan head 180 is shown in the illustration of FIG. 9. This scan head controls movement of the optical beam scan patterns along three axes 182, 184 and 186. A top 188 of the scan head 180 may be mounted to a surface of the aircraft, like the front underbelly of a helicopter or UAV, for example, such as shown in the sketch of FIG. 3. A window area 190 of the scan head 180 through which the beam scans are emitted would be pointed in the direction of movement or flight path of the aircraft. The fiber optic cable bundle of the optical paths 20 and 26 may be passed through a hole in the skin of the aircraft and into the scan head 180 through an opening 192 at the top 188 thereof. The optical elements within the scan head 180 which will be described in greater detail herein below cause the beams passed by the path 20 to be scanned 360° about the axis 186. A conventional motor assembly (not shown) within the scan head 180 controls movement of a lower portion 194 thereof ±90° about the axis 182 azimuthally with respect to the flight path of the aircraft. This movement occurs along a seam 196 between the top and bottom portions, 188 and 194, respectively, and effectively moves the axis 186 along with the lower portion 194 which projects the beam scan pattern through a helical pattern much the same as that described in connection with the example of FIG. 6.

Another portion 198 of the scan head 180 which includes the window area 190 and falls within the portion 194 moves azimuthally with the portion 194. Another conventional motor (not shown) disposed within the scan head 180 controls movement of the portion 198 about the axis 184+30° to −90° in elevation, for example, with respect to the flight path or heading of the aircraft. This movement causes the axis 186 and scan patterns to move in elevation with the portion 198. In the present embodiment, the window area 190 of the portion 198 may be controlled to move upward and inside the portion 194 to protect it from the environment when not in use. The corrugated skin or surface in the area 200 at the top portion 188 acts as a heat sink to improve the transfer of heat away from the scan head 180 during operation thereof.

Figure 10:
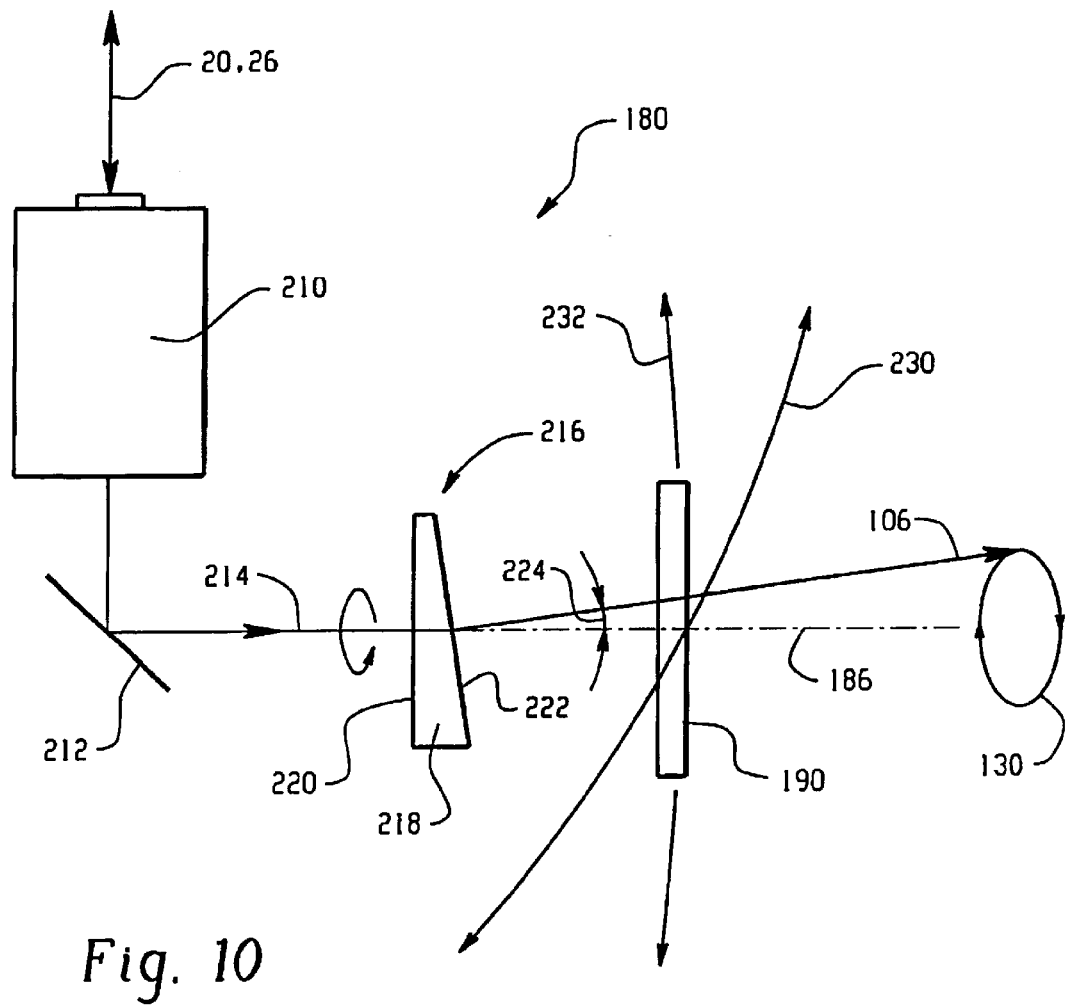
FIG. 10 is a sketch exemplifying suitable optical elements for use in the scan head embodiment of FIG. 9.

A sketch exemplifying suitable optical elements inside the scan head 180 is shown in FIG. 10. Referring to FIG. 10, the fiber optic cabling of the optical paths 20, 26 is aligned with the axis of the input aperture of a beam expander 210, if used in the present embodiment. The beam exiting the expander 210 may be reflected from a fold mirror 212 over an optical path 214 and passed into a rotating optical element 216. In the present embodiment, the rotating optical element 216 comprises a rotating optical wedge element 218 centered and rotated about the axis 186 and having a flat surface 220 at its input side and a surface 222 inclined at a predetermined angle at its output side. It is understood that other elements may be used for the rotating optical element 216, like an optical vibrator or resonator or a transparent liquid crystal scanner, for example, without deviating from the broad principles of the present invention.

The beam conducted over path 214 is aligned with the axis 186 and passed from the input side to the output side of the wedge element 218. The light beam is refracted in its path through the wedge element 218 and exits perpendicular to the inclined output surface 222 thereof. This refraction of the light beam causes it to exit the scan head 180 as beam 106 through the window area 190 at an angle 224 to the axis 186. Accordingly, as the wedge optical element 218 is rotated 360° about the axis 186, the beam 106 is projected conically from the scan head 180 to form the scan pattern 130 as described supra.

Backscattered light will follow the same optical paths as their emitted beams as described herein above. The window area 190 may comprise a clear, flat, zero power optical element made of a material like fused silica, for example, so as not to interfere substantially with the scan pattern of the exiting beam 106. In the present embodiment, the wedge optical element 218 and window 190 are structurally coupled to move together along the azimuth path 230 and elevation path 232 to cause the optical axis 186 to move along therewith. In this manner, the scan pattern 130 is forced to move in azimuth and elevation with the portions 194 and 198 of the scan head 180. Note that if an optical resonator is used in place of the rotating wedge, the resulting scan pattern will become sinusoidal as moved azimuthally.

Figure 11:
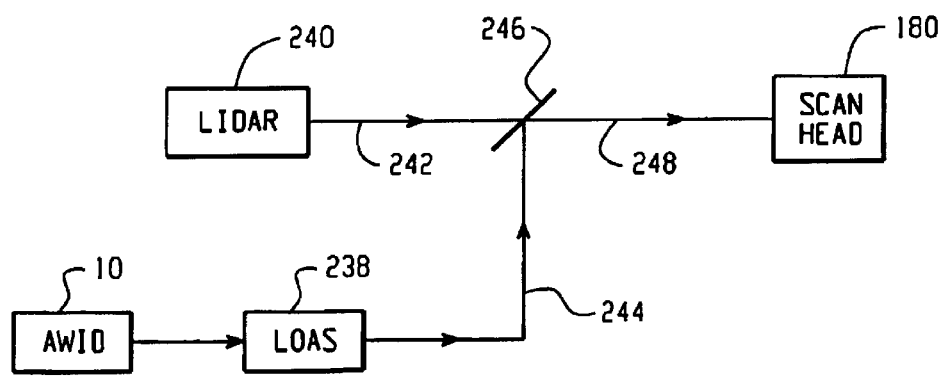
FIG. 11 is a block diagram schematic of yet another embodiment of the present invention.

An embodiment of a laser object awareness system (LOAS) 238 and a light detection and ranging (LIDAR) system 240 disposed on-board an aircraft has been described in the above referenced copending application Ser. No. 09/946,057, which has been incorporated by reference herein. The LOAS 238 and LIDAR 240 may utilize certain common optical elements, like the scanning module 100 which may be embodied in a scan head 180 remotely located from the optical elements of the LOAS 238 and LIDAR system 240 such as shown in the exemplary block diagram schematic of FIG. 11. In the embodiment of FIG. 11, the optical elements of 238 and 240 may be disposed within the aircraft and well supported and protected from the external environment thereof. Conventional fiber optic cabling may be used for the output optical paths 242 and 244 from the LIDAR 240 and LOAS 238, respectively, leading to and aligned with a dichroic filter optical element 246, for example, which may be used for combining the two systems. A further fiber optic cable provides for an optical path 248 from the dichroic filter 246 to the scan head 180 which includes the common optical elements. Note that the light beam output from the LIDAR 240 is passed by the dichroic filter element 246 to the path 248 while the light beam output from the LOAS 238 is reflected by element 146 to the path 248. The fiber optic cabling for the optical path 248 may be bistatic and may take a circuitous route within the aircraft to reach the scan head 180 which may be mounted to the external surface of the aircraft to permit the beam scan patterns of both of the LOAS 238 and LIDAR 240 to be projected out from the aircraft. More than one scan head may be used in the present embodiment without deviating from the present embodiment.

The AWID system 10 as described herein above may be added to and utilize certain common optical elements of the LOAS 238 and/or LIDAR 240 optical systems. For example, in the embodiment depicted in FIG. 11, the AWID system 10 is disposed on-board the aircraft and configured to utilize the optical path 244, optical element 246, optical path 248 and scanning module 180 as described herein above. In this embodiment, additional optical fibers may be included in the optical paths 244 and 248 to accommodate the paths 20 and 26 of the AWID system 10. In this configuration, the light beam of the AWID system 10 may be projected forward into the airspace in front of the aircraft by the scan module(s) 180 in the same scan pattern as the light beam of the LOAS 238 and/or light beam of the LIDAR 240, for example. Thus, if incorporated into a combined LOAS and LIDAR system, the AWID system 10 may add long or short range icing predictions along with the airspeed and obstacle detection already provided from the combined LOAS and LIDAR system.

While the present invention has been described in connection with one or more embodiments herein above, it is understood that these embodiments merely exemplify the present invention and are not to be used to limit the invention in any way, shape or form. Rather, the present invention should be construed in broad scope and breadth in accordance with the recitation of the appended claims hereto.

What is claimed is:

1. A warning system mountable on board an aircraft for inflight monitoring of the airspace ahead of the aircraft for conditions likely to cause ice accretion on the surface of the aircraft and provide a warning thereof, said system comprising:
   a laser source for generating a pulsed laser beam at a first wavelength;
   a first plurality of optical elements configured to direct said pulsed laser beam into the airspace ahead of the aircraft;

a second plurality of optical elements for receiving the backscattering of light from said pulsed laser beam, said second plurality of optical elements configured to separate the received backscattering of light into a plurality of predetermined wavelengths;

a plurality of light detectors for detecting the light of the separated plurality of wavelengths, respectively, and generating respectively corresponding plurality of electrical signals representative of the light detected thereby; and a processor for processing said plurality of electrical signals to determine if airspace conditions ahead of the aircraft are likely to cause ice accretion on the surface of the aircraft, and for generating a warning indicative thereof.

2. The system of claim 1 wherein the processor is operative to receive a temperature signal representative of the temperature of the airspace and process said temperature signal along with the plurality of electrical signals to determine if airspace conditions ahead of the aircraft are likely to cause ice accretion on the surface of the aircraft and the rate at which said ice accretion is likely to occur.

3. The system of claim 1 wherein the processor is operative to receive a speed signal representative of the speed of the aircraft and process said speed signal along with the plurality of electrical signals to determine if airspace conditions ahead of the aircraft are likely to cause ice accretion on the surface of the aircraft and the rate at which said ice accretion is likely to occur.

4. The system of claim 1 wherein the second plurality of optical elements includes: a first optical element for separating light substantially at the first wavelength from the received backscattering of light; and a second optical element for separating the separated light at the first wavelength into first and second polarization states; wherein the plurality of light detectors include: a first light detector for detecting the separated light of the first polarization state and generating a first electrical signal representative thereof; and a second light detector for detecting the separated light of the second polarization state and generating a second electrical signal representative thereof; and wherein the processor is operative to process the first and second electrical signals to determine the likelihood of ice accretion in the airspace.

5. The system of claim 4 wherein the processor is operative to determine a form of the water present in the airspace based on the ratio of the first and second electrical signals.

6. The system of claim 4 wherein the second plurality of optical elements further includes: a third optical element for separating light substantially at a second wavelength and light substantially at a third wavelength from the received backscattering of light; said light at said second wavelength being representative of a quantity of water molecules present in the airspace and said light at said third wavelength being representative of a quantity of air molecules present in the airspace; wherein the plurality of light detectors include: a third light detector for detecting the separated light at the second wavelength and generating a third electrical signal representative thereof; and a fourth light detector for detecting the separated light at the third wavelength and generating a fourth electrical signal representative thereof; and wherein the processor is operative to process the first, second, third and fourth electrical signals to determine the likelihood of ice accretion in the airspace.

7. The system of claim 6 wherein the processor is operative to determine a measure of water to dry air in the airspace based on a ratio of said third and fourth electrical signals and a measure of aerosols in the airspace based on a ratio of a combination of the first and second electrical signals and the fourth electrical signal.

8. The system of claim 1 wherein the second plurality of optical elements includes: a third optical element for separating light substantially at a second wavelength and light substantially at a third wavelength from the received backscattering of light; said light at said second wavelength being representative of a quantity of water molecules present in the airspace and said light at said third wavelength being representative of a quantity of air molecules present in the airspace; wherein the plurality of light detectors include: a third light detector for detecting the separated light at the second wavelength and generating a third electrical signal representative thereof; and a fourth light detector for detecting the separated light at the third wavelength and generating a fourth electrical signal representative thereof; and wherein the processor is operative to process the third and fourth electrical signals to determine the likelihood of ice accretion in the airspace.

9. The system of claim 8 wherein the processor is operative to determine a measure of water to dry air in the airspace based on a ratio of said third and fourth electrical signals.

10. The system of claim 1 wherein the first plurality of optical elements includes an optical scanner operative to scan the pulsed laser beam into the airspace with a predetermined pattern.

11. The system of claim 1 including an optical element for collecting the backscattering of light and focusing the collected light along an optical path directed to the second plurality of optical elements.

12. The system of claim 1 wherein the first plurality of optical elements is configured to direct the laser beam into the airspace substantially along a heading of the aircraft.

13. A warning system mountable on board an aircraft for inflight monitoring of the airspace ahead of the aircraft for conditions likely to cause ice accretion on the surface of the aircraft and provide a warning thereof, said system comprising:

a laser source for generating a pulsed laser beam at a first wavelength;

a first plurality of optical elements configured to direct said pulsed laser beam along a first optical path;

an optical scanner disposed in said first optical path and operative to scan said pulsed laser beam into the airspace ahead of the aircraft with a predetermined scan pattern, said scanner also operative to receive the backscattering of light from the pulsed laser beam and direct said backscattering along a second optical path;

a second plurality of optical elements for receiving the backscattering of light from said second optical path, said second plurality of optical elements configured to separate the received backscattering of light into a plurality of predetermined wavelengths;

a plurality of light detectors for detecting the light of the separated plurality of wavelengths, respectively, and generating respectively corresponding plurality of electrical signals representative of the light detected thereby; and a processor for processing said plurality of electrical signals to determine if airspace conditions ahead of the aircraft are likely to cause ice accretion on the surface of the aircraft, and for generating a warning indicative thereof.

14. The system of claim 13 wherein the optical scanner is operative to scan the scan pattern of the pulsed laser beam azimuthally in relation to the heading of the aircraft.

15. The system of claim 13 wherein the optical scanner is operative to scan the scan pattern of the pulsed laser beam in elevation in relation to the heading of the aircraft.

16. The system of claim 13 including means for determining the location of the laser beam in the predetermined scan pattern and generating a location signal indicative thereof; and wherein the processor is operative to process the plurality of electrical signals and the location signal to determine if airspace conditions ahead of the aircraft are likely to cause ice accretion on the surface of the aircraft and a location of said condition.

17. The system of claim 16 including a display for presenting data in a two dimensional image of the scanned airspace; and wherein the processor is operative to determine a value for the likelihood of ice accretion corresponding to each of a plurality of locations in the scanned airspace and to plot said likelihood values according to their associated locations in the two dimensional image of the display.

18. The system of claim 17 wherein the processor is operative to plot the likelihood values in a color coded format in the two dimensional image of the display.

19. The system of claim 13 wherein the first and second optical paths comprise fiber optic cables.

20. The system of claim 13 wherein the optical scanner comprises a scan head mountable to a surface of the aircraft remotely located from the first and second pluralities of optical elements.

21. The system of claim 20 wherein the first and second optical paths comprise fiber optic cables coupling the scan head optically to the first and second pluralities of optical elements.

22. The system of claim 13 wherein the optical scanner and certain optical elements of the warning system are common to a LIDAR system also mountable on-board the aircraft.

23. The system of claim 13 wherein the optical scanner and certain optical elements of the warning system are common to a laser obstacle awareness system (LOAS) also mountable on-board the aircraft.

* * * * *